United States Patent [19]

Hjorth et al.

[11] Patent Number: 4,466,957
[45] Date of Patent: Aug. 21, 1984

[54] VACCINE ADJUVANTS

[75] Inventors: Richard N. Hjorth, King of Prussia, Pa.; Bobby O. Moore, Fort Dodge, Iowa; Norman H. Grant, Wynnewood, Pa.

[73] Assignee: American Home Products Corporation, New York, N.Y.

[21] Appl. No.: 352,491

[22] Filed: Feb. 25, 1982

[51] Int. Cl.³ .................... A61K 39/02; A61K 39/12; A61K 39/145; A61K 39/245
[52] U.S. Cl. ....................................... 424/89; 424/88; 424/92
[58] Field of Search ............................ 424/88, 89, 92

[56] References Cited

U.S. PATENT DOCUMENTS 3,704,239 11/1972 Wei et al. ............................. 548/151
4,158,052 6/1979 Audibert et al. ...................... 424/89
4,214,089 7/1980 Fenichel et al. ..................... 548/151

FOREIGN PATENT DOCUMENTS 2287912 6/1976 France ................................. 424/89

OTHER PUBLICATIONS

Chemical Abstracts, vol. 94, No. 1, Abstract No. 4018a, 1981.
Chemical Abstracts, vol. 95, No. 1, Abstract No. 411w, 1981.
Chem. Abstr. 97: 84596n, (1982), of Michiels, Metal Methods Enzymol, (1982), 84, (Immunochem. Tech., Part 1), :542–551, Radio-Immunoassay of Dimozide.
Chem. Abstr. 94: 4018a, (1981), of Al Burn et al., U.S. Pat. 4,214,089, 22 Jul. 1980, Thiazolo[3,2-a]benzimidazoles etc . . . as . . . Enhancers of the Immune Response.
Chem. Abstr. 92: 33954s, (1980), of Warren, G. et al., Immunopharmacology, 1979, 1, (4), :269–276, Stimulation by a Hydroxythiazolo Benzimidazole of Enhanced Formation of Antibodies to Sheep Erythrocytes in Vitro and in Vivo.
Chem. Abstr. 89: 141183m, (1978), Warren et al., Experientia, (1978), 34, (6), :802–3, Immunomodulating Effects of a Hydroxythiazolo Benzimidazole.
Chem. Abstr. 89: 53363q, 1978, of Eur. J. Cancer, 1978, 144, 393–400, The Immunostimulatory Activity of 3-(-p-chlorophenyl)-2,3-dihydro-3-hydroxythiazole[3-,2-a]benzimidazole-2-acetic Acid.
Chem. Abstr. 87: 143863m, 1977, of Cancer Res, 1977, 37, (9), :3338–43, Association of Macrophase Activation with Antitumor Activity by Synthetic and Biological Agents . . . Adjuvants . . . Wy. 13876 . . . Typhoid Vaccine".
Chem. Abstr. 83: 37403y, 1975, of Michiels Life Science, 1975, 16, (6), 937–944, Radio Immunoassay of the Neuroleptic Drug Dimozide.

Primary Examiner—Shep K. Rose
Attorney, Agent, or Firm—George Tarnowski

[57] ABSTRACT

There are disclosed mammalian vaccine compositions comprising an inactivated whole or subunit vaccine or toxoid and an adjuvant having the formula

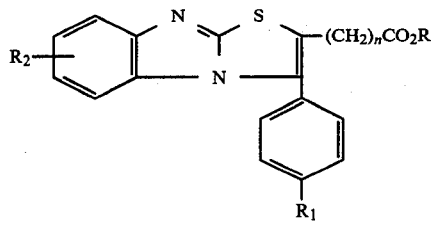

wherein R is hydrogen or lower alkyl, $R_1$ is hydrogen, lower alkyl, lower alkoxy, trifluoromethyl or halo, $R_2$ is hydrogen, chloro or nitro, n is 1 or 2 and pharmaceutically acceptable salts thereof.

3 Claims, No Drawings

VACCINE ADJUVANTS

At the present time, there exist four major categories of vaccines in general use: living vaccines, killed or inactivated whole organism vaccines, subunit vaccines and toxoids. Of all these, the living vaccines are able to induce the strongest level of immunity in the host. These vaccines, consisting of attenuated infectious organisms or their mutants, are highly effective because the host is able to mount a long-lasting immune response to the organisms, but the growth of the organism in the host is of such a sufficiently limited extent that no disease is produced in the host.

When proper living vaccines cannot be produced, killed vaccines are used. The living organisms are inactivated by chemical or other means, but even though the organisms are inactivated, the antigenic factors responsible for eliciting the immune response remain intact, so that the desired stimulation of immunity can be achieved. Examples of inactivated whole organism vaccines are the pertussis and Salk poliomyelitis vaccines.

In some instances, however, even killing the organism does not prevent it from causing effects in the recipient. In these cases, the agents must be fragmented into subfractions or subunits, thereby rendering them unharmful to the recipient. Examples of such subunit vaccines include some influenza vaccines and some experimental herpes virus and hepatitis vaccines. Finally, toxoid vaccines are those in which a toxin excreted by an organism is rendered nontoxic and is then used just as any other antigenic factor to stimulate an immune response to the toxin. Tetanus toxoid is an example of such a vaccine.

Unfortunately, the subunit and toxoid vaccines rarely furnish enough antigens to confer a long-lasting immunity in the host, so that the immunity induced by the nonliving vaccines, and especially the highly purified subunit vaccines is usually short-lived (1–2 years).

In order to strengthen the immune response elicited by nonliving vaccines, it is possible to inject the vaccine along with an adjuvant. There are a number of postulated mechanisms by which adjuvants are thought to enhance the immune response. In the case of adjuvants such as Freund's complete adjuvant (mineral oil, water, an emulsifier and killed tuberculosis bacteria), mechanical mechanisms as well as immune inspired mechanisms have been put forth. Thus, Freund's adjuvant can operate by depot formation, whereby the adjuvant traps the antigen and prevents it from being removed and degraded by the body allowing the antigenic stimulus to continue over a prolonged period of time. Any antigen that does escape the site is bound by lipophilicity in the oil droplets of the Freund emulsion and settles in the lymph nodes where it provides a further stimulus. The depot effect also operates with such well-known adjuvants as aluminum hydroxide and aluminum phosphate, which are especially used in diphtheria toxoid vaccines.

It has also been postulated that Freund's adjuvant increases the size of the antigen particle by trapping it in the oil droplets. This increases the antigen uptake by macrophages, a process which is usually the first step in antibody formation and othr immune responses.

Some adjuvants can enhance antibody formation by directly acting on the immune system, as for example, by attracting macrophages to the inoculation site and by drawing lymphocytes to the appropriate lymph nodes. Indeed, some studies have shown that when certain adjuvants are inoculated separately prior to administration of the antigen, the subsequent injection of antigen results in the same increased antibody formation as occurs with the simultaneous administration of adjuvant and antigen. It is postulated that the adjuvants have an effect on the immune system, stimulating the production of factors which result in a subsequent higher antibody response.

Of the many adjuvants available for use in mammals, only aluminum hydroxide and aluminum phosphate have seen widespread use in humans. Many potential adjuvants have been rejected for use in humans because they cause severe local or systemic reactions. Some of these, such as Freund's adjuvant which contains mineral oil, are nonmetabolizable and by causing cancer in laboratory animals are potentially carcinogenic. The need exists, therefore, to develop more effective and safe adjuvants which can potentiate the action of vaccines, especially the new subunit type vaccines which are currently being developed or which will be developed in the future.

The present invention is directed to a mammalian vaccine composition comprising an inactivated whole or subunit vaccine or toxoid and an adjuvant having the formula

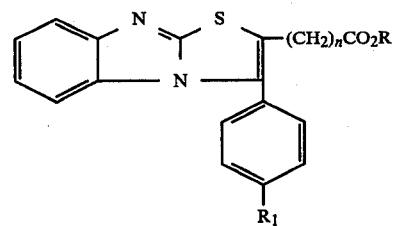

wherein R is hydrogen or lower alkyl, $R_1$ is hydrogen, lower alkyl, lower alkoxy, trifluoromethyl or halo, $R_2$ is hydrogen, chloro or nitro, n is 1 or 2 and pharmaceutically acceptable salts thereof.

The compounds of formula I and their method of preparation are disclosed in U.S. Pat. Nos. 4,214,089, and 3,704,239.

The term pharmaceutically acceptable salts includes the salts of pharmacologically-acceptable organic and inorganic acids such as hydrochloric, hydrobromic, sulfuric, nitric, phosphoric, methanesulfonic, benzenesulfonic and the like, alkali metal carboxylates and carboxylates of a pharmacologically acceptable cation derived from ammonia or a basic amine.

The alkali metal carboxylates of the invention can be prepared by mixing stoichiometrically equivalent amounts of the free acids, preferably in aqueous solution, with solutions of alkali metal bases, such as sodium potassium, and the lithium hydroxides or carbonates, and the like, then freeze drying the mixture to leave the product as a residue. The amine salts can be prepared by mixing the free acids, preferably in solution, with a solution of the appropriate amine, in water, isopropanol, or the like, and freeze drying the mixture to leave the product as a residue.

The terms "lower alkyl" and "lower alkoxy" when used herein and in the appended claims includes straight and branched chain hydrocarbon radicals and moieties having from 1 to about 6 carbon atoms, illustrative members of which are methyl, ethyl, n-propyl, i-propyl, n-butyl, t-butyl, n-pentyl, n-hexyl, 3-methylpentyl, 2,3-dimethylbutyl, and the like.

"Alkali metal" includes, for example, sodium, potassium lithium, and like. "Halo" includes fluoro, chloro, bromo and iodo. A "pharmacologically-acceptable cation derived from ammonia or a basic amine" contemplates the positively charged ammonium ion and analogous ions derived from organic nitrogenous bases strong enough to form such cations. Bases useful for the purpose of forming pharmacologically-acceptable non-toxic addition salts of such compounds containing free carboxyl groups form a class whose limits are readily understood by those skilled in the art.

The adjuvants used in the composition of the invention exhibit a marked immunomodulatory activity and it is postulated that the adjuvanting effect of these compounds is a direct result of their ability to modulate the immune response. Moreover, by virtue of their anti-tumor activity and lack of reactogenic potential, the suitability of the compounds as adjuvants for vaccines is even further enhanced.

The vaccines used in the composition of the invention can be veterinary or human vaccines, and include both inactivated whole and subunit vaccines as well as toxoids. Moreover, the vaccines employed are those used to immunize against bacterial, rickettsial and viral pathogens. Suitable human vaccines would include for example, the whole and subunit vaccines for influenza, poliomyelites, arbovirsus infections, typhoid and paratyphoid, ekolcra, plague, pertussis, typhus, Rocky Mountain spotted fever, Haermophilus influenzae type G, multivalent pneumococcal polysaccharide, meningococcal group C and the newly developed human diploid cell rabies vaccine and heptatitis vaccine.

Suitable veterinary vaccines would include, for example, the whole and subunit vaccines for equine influenza viruses, equine herpesviruses, equine encephalomyelitis viruses, wart virus, foot-and-mouth disease virus, rabies, feline panleukopenia, feline rhinotracheitis, feline calicivirus, infectious bovine rhinotracheitis, parainfluenza-3, bovine virus diarrhea, bovine adenoviruses, pseudorabies, transmissible gastroenteritis virus, porcine parvovirus, canine adenoviruses, canine distemper virus and canine parainfluenza. Whole and subunit vaccines, bacterins and toxoids for strangles, brucellosis, vibriosis, leptospirosis, clostridial infections, salmonellosis, colibacillosis, anaplasmosis, pasteurella infections, haemophilus infections, erysipelothrix and the like. Further, it is fully contemplated that since the vaccines of the future, especially the viral and bacterial subunit types, may likely be weak immunogens, they will require potentiation via a suitable and acceptable adjuvant, and it is felt that the system of the present invention will be highly suitable.

The advantages of using the disclosed potent adjuvants with vaccines are significant. By modulating certain compartments of the immune system, the adjuvants can cause an increase in the immune reactivity of the humoral immunity, resulting in potentiated antibody production to the antigenic material contained in the vaccine preparation with which the adjuvants are administered to the recipient. Such potentiation, of course, will permit stronger and longer levels of immunity to be achieved, even though the immunizing agent may be a weak immunogen, such as may be found with many of the inactivated whole and especially the subunit vaccines and toxoids. This potentiation of immune response to antigen has as a direct result of this effect, the further advantage that it is possible to use less immunizing antigenic material thereby decreasing the potential for serious and stressful host reactions to the immunization. This is particularly important in the vaccinations of juveniles. Moreover, in addition to making immunizations more successful and thus safer with a reduced dose of purified antigen, vaccine production can be made more economical and more feasible.

The compositions of the invention are prepared by dissolving or suspending the adjuvant material in the antigen diluent and then combining suitable volumes of the adjuvant solution and the antigen solution at the appropriate antigen dilution. The antigen diluents are those conventional in the art, such as phosphate buffered saline, minimum essential medium, peptone and the like. The dose of adjuvant employed in the composition is based on the body weight to the vaccine recipient and a suitable range for the adjuvants used in the invention is about 10–50 mg/kg.

The adjuvanting activity of adjuvant used in the composition of the invention is demonstrated using a standard antigen extinction test using a whole inactivated equine herpesvirus 1 vaccine and subunit human influenza A/Bangkok vaccine. These experiments are presented immediately after the following examples which show the preparation of some of the adjuvants used in the composition of the invention.

EXAMPLE 1

3-(p-Chlorophenyl)-Thiazolo[3,2-a]Benzimidazole-2-Acetic acid 3-(p-Chlorophenyl)-2,3-dihydro-3-hydroxy-thiazolo[3,2-a]-benzimidazole-2-acetic acid, (5.0 g.) is suspended in a solution of 100 ml. of a 6N NCl and 200 ml. of dioxane. The mixture is heated at reflux for 18 hours. The solution is concentrated in vacuo to 50 ml. To the concentrate is added 200 ml. of water, and sufficient 4N NaOH solution to dissolve all the solids. The alkaline solution is made acidic with acetic acid. The solid is collected, washed well with water and airdried. The crude material is recrystallized from dimethoxyethane. The product (2.0 g.) melts at 242°–243° C.

Analysis for: $C_{17}H_{11}ClN_2O_2S$: Calculated: C, 59.56; H, 3.24; Cl, 10.34; N, 8.17; S, 9.36; Found: C, 59.28; H, 3.40; Cl, 11.00; N, 8.03; S, 9.93.

EXAMPLE 2

To prepare: 3-phenyl-thiazolo[3,2-a]benzimidazole-2-acetic acid, treat 3-phenyl-2,3-dihydro-3-hydroxy-thiazolo[3,2-a]benzimidazole-2-acetic acid as taught in Example 1.

EXAMPLE 3

To prepare: 3-[3-(p-bromophenyl)-thiazolo[3,2-a]benzimidazole-2-yl]-propionic acid, treat 3-[3-(p-bromophenyl)-2,3-dihydro-3-hydroxythiazolo[3,2-a]benzimidazole-2-yl]-propionic acid as taught in Example 1.

EXAMPLES 4–8

Following the procedure of Example 1, there are prepared the following compounds:

| Example | Compound | Melting Point |
|---------|----------|---------------|
| 4 | 3-(p-Fluorophenyl)-thiazolo[3,2-a]-benzimidazole-2-acetic acid | 240–250° C. dec. |
| 5 | 3-(p-Bromophenyl)-thiazolo[3,2-a]-benzimidazole-2-acetic acid | 245–247° C. |

-continued

| Example | Compound | Melting Point |
|---|---|---|
| 6 | 3-(p-Methoxyphenyl)-thiazolo[3,2-a]-benzimidazole-2-acetic acid | 275° C. dec. |
| 7 | 3-(p-Methylphenyl)-thiazolo[3,2-a]-benzimidazole-2-acetic acid | 274–280° C. dec. |
| 8 | 3-(p-Trifluoromethylphenyl)-thiazolo-[3,2-a]benzimidazole-2-acetic acid | 255–256° C. dec. |

EXAMPLE 9

The equine herpesvirus 1 (EHV-1) antigen extinction vaccination and challenge test measures the ability of the adjuvant to enhance the protective immune response of hamsters to the EHVI test antigen as determined by a lethal EHVI challenge inoculation.

Initially the following two-fold dilutions of inactivated ENV-1 vaccine virus are prepared in 2% peptone solution: 6.25, 12.5, 25, 50 100, 200 and 400. The adjuvant is then prepared in the test antigen diluent at twice the concentration desired per ml of final vaccine. The final vaccine is then prepared by mixing a constant volume of each antigen dilution with an equal volume of adjuvant solution or diluent control. Because of this preparation procedure, the final test antigen dilution series is 12.5, 25, 50, 100, 200, 400 and 800.

For each adjuvant-antigen dilution composition, five outbred golden Syrian male ELa;ENG hamsters, approximately 5–7 weeks of age, are each vaccinated intramuscularly in the hind leg with a 0.2 ml dose. At the time of vaccination, ten additional hamsters from the same group as the vaccinates are held as unvaccinated controls. Subsequent to vaccination, the vaccinated and unvaccinated control hamsters are held 21 days before challenging.

Three weeks after vaccination, all the animals are challenged intraperitoneally with 0.1 ml of the challenge virus use-dilution, which has an average titer of 5 $\log_{10}$ hamster $LD_{50}$/0.1 ml. Following challenge, all hamster deaths occurring in the vaccinates and unvaccinated controls are recorded daily for 7 days post challenge. The challenge virus is a hamster liver suspension of a highly virulent hamster-adapted strain of EHV-1 virus. The challenge virus-use dilution has proven to be >99% lethal to all unvaccinated control hamsters injected.

The mortality of the inoculated animals is recorded, and the hamster protective endpoint is expressed as that dilution of EHV-1 antigen + diluent control or adjuvant which "protects" 50% of the hamsters against the test dose of EHV-1 challenge virus. The Reed-Muench formula for calculating 50% serum neutralization end point is used. The results are expressed as the anti-log of the 50% protective antigen dilution.

In the results presented below, the test adjuvant A is 3-(p-chlorophenyl)thiazolo[3,2-a]benzimidazole-2-acetic acid. 50 mg of adjuvant A is dissolved in 10 ml of a 2% peptone solution to give an adjuvant working solution of 5 mg/ml. Adjuvanted antigen dilutions are prepared by mixing 1 ml of each antigen dilution with 1 ml of the 5 mg/ml solution. The following dilutions containing 2.5 mg/ml of adjuvant A are prepared: 12.5, 25, 50, 100 and 200.

The results of the test are summarized below:

| Antigen Dilution | Diluent Control | Positive Control ($AlPO_4$ 10 mg/kg) | Adjuvant A |
|---|---|---|---|
| 12.5 | 1/5* | 0/5 | 0/5 |
| 25.0 | 3/5 | 1/5 | 2/5 |
| 50.0 | 4/5 | 1/5 | 2/5 |
| 100.0 | 5/5 | 1/5 | 2/5 |
| 200.0 | | 3/5 | 5/5 |
| 400.0 | | 5/5 | |
| | | Unvaccinated controls: 10/10 | |

* = Hamster Deaths/Vaccinates challenged

Antigen hamster protective dose 50 ($AHPD_{50}$):
Diluent control = 22.38
Adjuvant A = 64.85
Positive Control = 132

It is clear from the results that adjuvant A stimulated a definite protective response in the vaccinated animals, evidencing adjuvant activity.

EXAMPLE 10

In this experiment varying doses of the adjuvant, 3-(p-chlorophenyl)thiazolo[3,2-a]benzimidazole-2-acetic acid in sterile pyrogen-free saline, are mixed with a 1:50 dilution of influenza A/Bangkok monovalent vaccine concentrate and injected intraperitoneally into male Swiss mice. After 35 days, the mice are bled and hemagglutination inhibition titers against influenza A/-Bangkok are determined. The results are presented below:

| Group | Day of Adjuvant | Dosage of Adjuvant | Anti-influenza Ab Titers for Each Mouse | Geom. Mean |
|---|---|---|---|---|
| Experiment No. 1 | | | | |
| 1 | −1 | 125 mg/Kg | 64, 128, 64, 40 | 68 |
| 2 | 0 | " | 128, 64, 64, 128 | 91 |
| 3 | +1 | " | 32, 128, 64, 32 | 54 |
| 4 | 0 | 312.5 mg/Kg | dead | — |
| 5 | no adjuvant | — | <8, <8, <8, <8 | 4 |
| 6 | no vaccine or adjuvant | — | <8, <8, <8, <8 | 4 |
| Experiment No. 2 | | | | |
| 1 | −1 | 5 mg/Kg | 40, 40, 20, <8 | 19 |
| 2 | 0 | " | <8, 20, 40, <8 | 11 |
| 3 | +1 | " | 64, 64, <8, <8 | 16 |
| 4 | 0 | 25 mg/Kg | 32, 64, 64, 128 | 64 |
| 5 | no adjuvant | — | 10, 40, <8, <8 | 9 |
| 6 | no vaccine or adjuvant | — | <8, <8, <8, <8 | 4 |
| Experiment No. 3 | | | | |
| 1 | 0 | 312.5 mg/Kg | 64, 128 | 91 |
| 2 | 0 | 125 mg/Kg | 40, <8, 128, 64 | 34 |
| 3 | vaccine only | — | <8, <8, <8, <8 | 4 |
| 4 | adjuvant only | 312.5 mg/Kg | 10, <10 | 6 |
| Experiment No. 4 | | | | |
| 1 | 0 | 0 | 10, <10, 10, 20 | 10 |
| 2 | 0 | 5 | 20, 10, 10, 10 | 12 |
| 3 | 0 | 10 | 128, 64, 256, <10 | 57 |
| 4 | 0 | 25 | 64, 32, 32, <10 | 24 |

The results show that at adjuvant levels above 10 mg/kg, the antibody response is very strongly enhanced and that this effect occurs at adjuvant levels as high as 312.5 mg/kg.

EXAMPLE 11

In this experiment various adjuvants or phosphate buffered saline (PBS) are mixed with an equal volume of dilutions of influenza A/Bangkok monovalent vaccine concentrate and injected intramuscularly in 0.5 ml doses into male Swiss mice. After 35 days, the mice are bled and hemagglutination inhibition titers against influenza A/Bangkok are determined. The results are presented below:

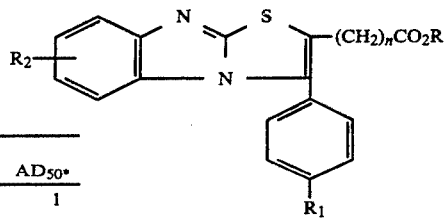

| Group | Vaccine Dilution | Adjuvant | Anti-influenza Ab Titers for Each Mouse | Geom. Mean | AD50* |
|---|---|---|---|---|---|
| I | Undil. | PBS | 16, <8, <8, 32, <8, <8 | 7.1 | 1 |
| | 1:5 | " | <8, <8, <8, <8, 20, 32 | 6.2 | |
| | 1:25 | " | <10, 20, <8, 32, 20, 20 | 13.1 | |
| | 1:125 | " | 40, 20, <8, <8, 8, 16 | 8.2 | |
| | 1:625 | " | <8, 32, 16, <8, <8, 16 | 9.0 | |
| | 1:3125 | " | <8, <8, <8, <8, <10, <8 | 4.2 | |
| II | Undil. | A 25 mg/Kg final | 16, 64, 16, 64, 64, 8 | 28.5 | 2529 |
| | 1:5 | A 25 mg/Kg final | 32, 64, 128, 64, 64, 64, | 64.0 | |
| | 1:25 | A 25 mg/Kg final | 32, 32, 64, 32, <8, 32 | 25.4 | |
| | 1:125 | A 25 mg/Kg final | 32, 20, 256, 10, 20, 10 | 26.3 | |
| | 1:625 | A 25 mg/Kg final | 20, <8, 64, 20, 64, 20, | 14.2 | |
| | 1:3125 | A 25 mg/Kg final | 64, <8, 20, <8, <8, <8 | 8.3 | |
| III | Undil. | Freunds Complete adjuvant | <8, 32, 20, <8, 64, 10 | 13.7 | 22 |
| | 1:5 | Freunds Complete adjuvant | <8, 512, 512, 512, <8, <8 | 45.3 | |
| | 1:25 | Freunds Complete adjuvant | 40, <8, 20, 40, <8, <8 | 11.3 | |
| | 1:125 | Freunds Complete adjuvant | 16, 128, <8, <8, 256, 20 | 23.5 | |
| | 1:625 | Freunds Complete adjuvant | <8, 64, <8, 16, <8, <8 | 8 | |
| | 1:3125 | Freunds Complete adjuvant | <8, <8, <8, <8, <8, <10 | 4.2 | |
| IV | Undil. | AlPO4 5 mg/ml final | 32, 20, 128, 64, 64, 20 | 43.4 | 1918 |
| | 1:5 | AlPO4 5 mg/ml final | 20, 32, 64, 16, 32, 20 | 27.4 | |
| | 1:25 | AlPO4 5 mg/ml final | 128, 64, 32, 16, 32, 32 | 40.3 | |
| | 1:125 | AlPO4 5 mg/ml final | 40, <8, 20, 32, 64, <8 | 17.2 | |
| | 1:625 | AlPO4 5 mg/ml final | 128, 128, <8, <8, 16, 32 | 22.6 | |
| | 1:3125 | AlPO4 5 mg/ml final | 16, <8, 10, 128, <8, <8 | 10.5 | |

*Antigenic Dose$_{50}$; the dilution of antigen which causes seroconversion in 50% of the mice as calculated by Probin analysis.
A = 3-(p-chlorophenyl)thiazolo[3,2-a]benzimidazole-2-acetic acid.

The results show that the adjuvant of the invention is able to potentiate the immune response to influenza subunit vaccine.

What is claimed is:

1. A mammalian vaccine composition comprising an inactivated whole or subunit virus vaccine and an effective amount of an adjuvant having the formula wherein R is hydrogen or 1 to 6 carbon atom lower alkyl, $R_1$ is hydrogen, 1 to 6 carbon atom lower alkyl, 1 to 6 carbon atom lower alkoxy, trifluoromethyl or halo, $R_2$ is hydrogen, chloro or nitro, n is 1 or 2 and pharmaceutically acceptable salts thereof.

2. The composition of claim 1 wherein said vaccine is inactivated whole equine herpesvirus 1 and said adjuvant is 3-(p-chlorophenyl)thiazolo[3,2-a]benzimidazole-2-acetic acid.

3. The composition of claim 1 wherein said vaccine is subunit influenza A and said adjuvant is 3-(p-chlorophenyl)thiazolo[3,2-a]benzimidazole-2-acetic acid.

* * * * *